US010022416B2

(12) United States Patent
Sripathy et al.

(10) Patent No.: US 10,022,416 B2
(45) Date of Patent: Jul. 17, 2018

(54) HIGHLY BIOAVAILABLE, WATER SOLUBLE AND SUSTAINED RELEASE NANOFORMULATIONS HYDROPHOBIC PLANT DERIVED COMPOUNDS AND EXTRACTS

(71) Applicant: LAILA PHARMACEUTICALS PVT. LTD., Vijayawada (IN)

(72) Inventors: Ravichandran Sripathy, Vijayawada (IN); Venkata Narasimha Siva Rama Raju Mandapati, Vijayawada (IN); Gopaal Ajay, Vijayawada (IN); Nirvanashetty Somashekara, Vijayawada (IN); Ramchand Nanappan Chaniyilparampu, Vijayawada (IN); Rama Raju Gokaraju, Vijayawada (IN); Ganga Raju Gokaraju, Vijayawada (IN); Kiran Bhupathiraju, Vijayawada (IN); Dwarakanath Anjana, Vijayawada (IN)

(73) Assignee: Laila Pharmaceuticals PVT. LTD., Vijayawada (IN)

( * ) Notice: Subject to any disclaimer, the term of this patent is extended or adjusted under 35 U.S.C. 154(b) by 15 days.

(21) Appl. No.: 14/540,212

(22) Filed: Nov. 13, 2014

(65) Prior Publication Data
US 2015/0072012 A1 Mar. 12, 2015

Related U.S. Application Data

(63) Continuation-in-part of application No. PCT/IN2013/000328, filed on May 21, 2013.

(30) Foreign Application Priority Data

May 22, 2012 (IN) .......................... 2019/CHE/2012

(51) Int. Cl.

| | |
|---|---|
| *A61K 36/9066* | (2006.01) |
| *A61K 9/51* | (2006.01) |
| *A61K 9/00* | (2006.01) |
| *A61K 9/10* | (2006.01) |
| *A61K 9/107* | (2006.01) |
| *A61K 36/9068* | (2006.01) |
| *A61K 36/16* | (2006.01) |
| *A61K 36/185* | (2006.01) |
| *A61K 36/258* | (2006.01) |
| *A61K 36/38* | (2006.01) |
| *A61K 36/53* | (2006.01) |
| *A61K 31/12* | (2006.01) |
| *A61K 31/047* | (2006.01) |
| *A61K 31/05* | (2006.01) |
| *A61K 31/122* | (2006.01) |
| *A61K 31/19* | (2006.01) |
| *A61K 31/353* | (2006.01) |
| *A61K 31/366* | (2006.01) |
| *A61K 31/704* | (2006.01) |
| *A61K 47/10* | (2017.01) |
| *A61K 47/26* | (2006.01) |

(52) U.S. Cl.
CPC ........ *A61K 36/9066* (2013.01); *A61K 9/0053* (2013.01); *A61K 9/10* (2013.01); *A61K 9/1075* (2013.01); *A61K 31/047* (2013.01); *A61K 31/05* (2013.01); *A61K 31/12* (2013.01); *A61K 31/122* (2013.01); *A61K 31/19* (2013.01); *A61K 31/353* (2013.01); *A61K 31/366* (2013.01); *A61K 31/704* (2013.01); *A61K 36/16* (2013.01); *A61K 36/185* (2013.01); *A61K 36/258* (2013.01); *A61K 36/38* (2013.01); *A61K 36/53* (2013.01); *A61K 36/9068* (2013.01); *A61K 47/10* (2013.01); *A61K 47/26* (2013.01); *A61K 9/51* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 4,996,004 A * | 2/1991 | Bucheler .................. | A61K 8/06 366/340 |
| 2003/0165438 A1 | 9/2003 | Benham | |
| 2004/0131710 A1* | 7/2004 | Seiberg et al. ............... | 424/757 |
| 2004/0258744 A1 | 12/2004 | Counsell | |

(Continued)

FOREIGN PATENT DOCUMENTS

| | | | |
|---|---|---|---|
| WO | 2010010431 A1 | 1/2010 | |
| WO | WO 2010070665 A2 * | 6/2010 | |
| WO | 2010106191 A1 | 9/2010 | |
| WO | WO 2010106191 A1 * | 9/2010 | ........... A61K 9/4858 |
| WO | WO-2012024405 A2 * | 2/2012 | ............... A61K 9/06 |

OTHER PUBLICATIONS

ICI Americas Inc. "The HLB System: A Time-Saving Guide to Emulsifier Selection." ICI Americas Inc. Wilmington, DE, Revised Mar. 1980, pp. 1-22.*

(Continued)

*Primary Examiner* — Isaac Shomer
(74) *Attorney, Agent, or Firm* — Kramer Amado, P.C.

(57) ABSTRACT

A highly bioavailable, water soluble, sustained release nanoformulation comprising a hydrophobic plant derived compound(s) in an emulsifier phase, and aqueous phase. The formulation provides sustained release of the hydrophobic plant derived compound(s) over a 24 hr time period. A process for preparation of the water soluble nanoformulation is described.

21 Claims, 5 Drawing Sheets

(56) References Cited

U.S. PATENT DOCUMENTS

| | | | |
|---|---|---|---|
| 2008/0199523 A1* | 8/2008 | Finnie et al. | 424/484 |
| 2008/0255247 A1* | 10/2008 | Sagalowicz et al. | 514/772 |
| 2009/0136435 A1* | 5/2009 | Mulvanerty | A61K 9/0014 424/59 |
| 2009/0297665 A1* | 12/2009 | Bromley | A23L 1/30 426/72 |
| 2010/0227828 A1* | 9/2010 | Gokaraju | A61K 8/602 514/27 |

OTHER PUBLICATIONS

L Zhongfa, M Chiu, J Wang, W Chen, W Yen, P Fan-Havard, LD Yee, KK Chan. "Enhancement of curcumin oral absorption and pharmacokinetics of curcuminoids and curcumin metabolites in mice." Cancer Chemotherapy and Pharmacology, vol. 69, 2012, pp. 679-689, published online Oct. 4, 2011.*

V Madaan, A Chanana, MK Kataria, A Bilandi. "Emulsion Technology and Recent Trends in Emulsion Applications." International Research Journal of Pharmacy, vol. 5(7), 2014, pp. 533-542.*

United States Court of Appeals for the Federal Circuit. "In re James F. Crish and Richard L. Eckert." 04-1075, U.S. Appl. No. 08/822,509. Decided Dec. 21, 2004, pp. 1-12.*

Material Safety Sheet for Castol Oil, Ethoxylated, Spectrum. Gardena, CA; New Brunswick, NJ.

Gelderblom, et al., "Cremophor EL: the drawbacks and advantages of vehicle selection for drug formulation", European Journal of Cancer 37 (2001) 1590-1598.

* cited by examiner

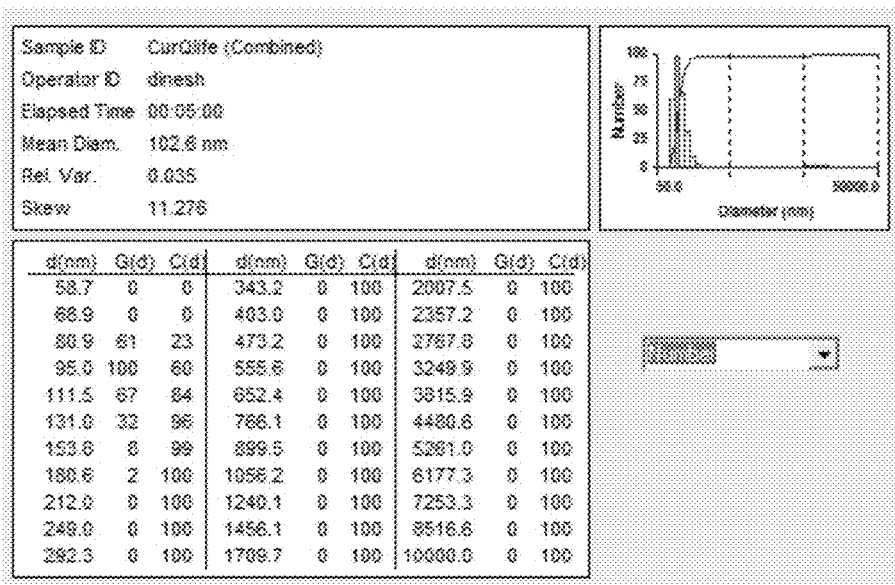
Fig. 1: Malvern Particle Size analysis of CurQlife®.
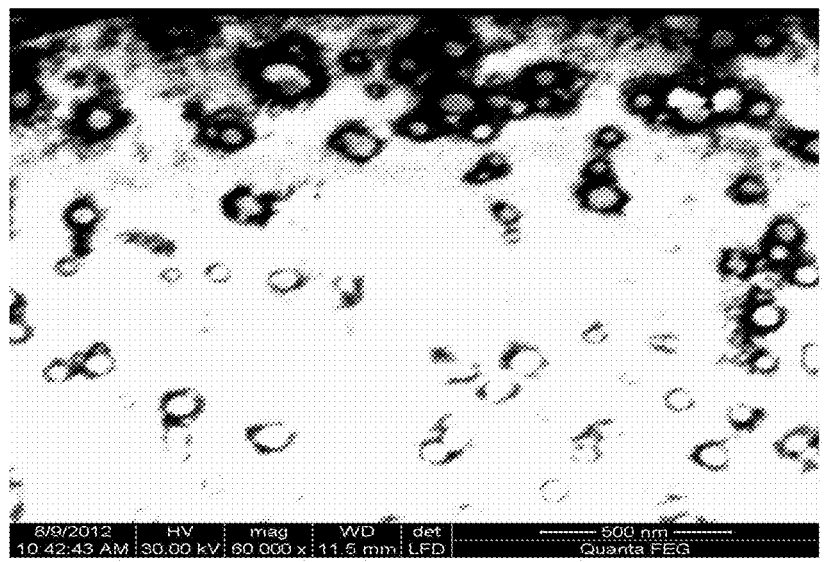
Fig. 2: Morphological Characterization of CurQlife by Scanning Electron Microscopy (SEM).

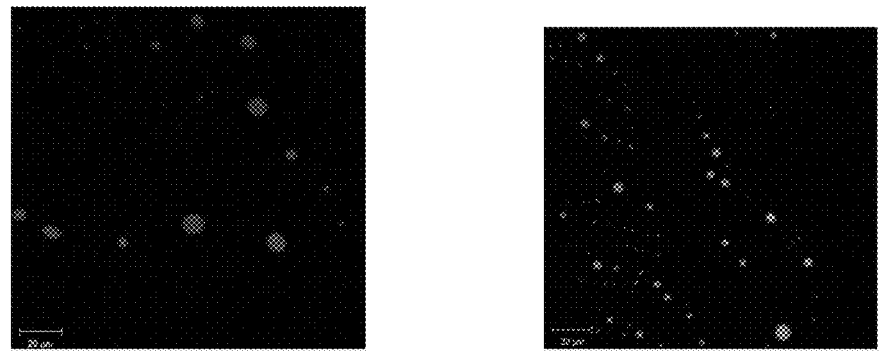
Fig. 3: Confocal Microscopy of CurQlife
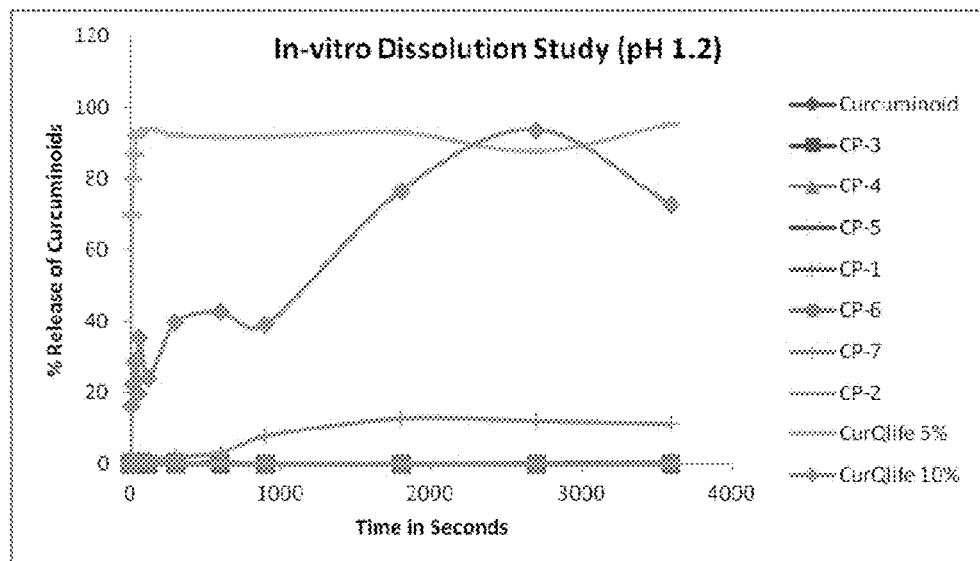
Fig. 4: Preliminary dissolution study (pH-1.2) results of CurQlife® in comparison with other curcuminoid products in the market.

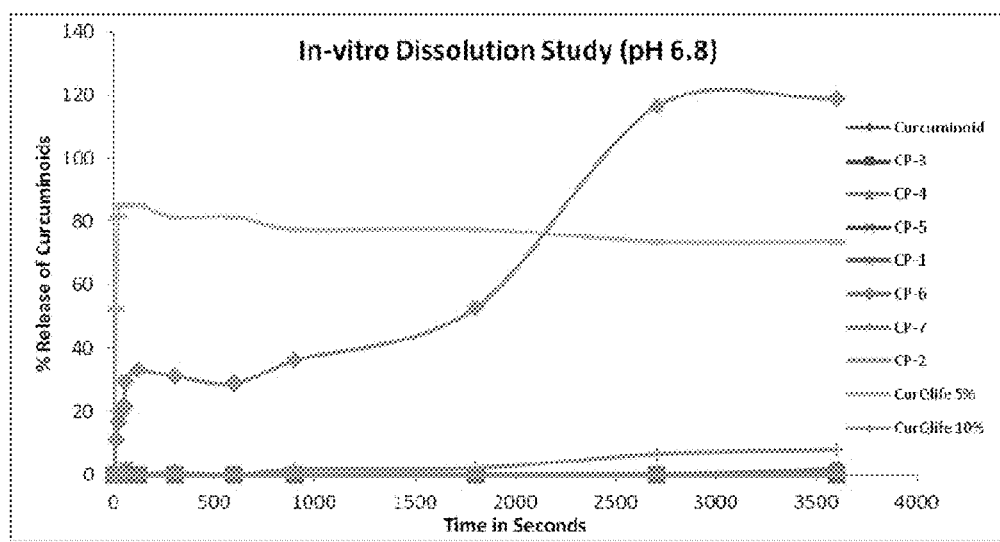
Fig. 5: Preliminary dissolution study (pH-6.8) results of CurQlife® in comparison with other curcuminoid products in the market.

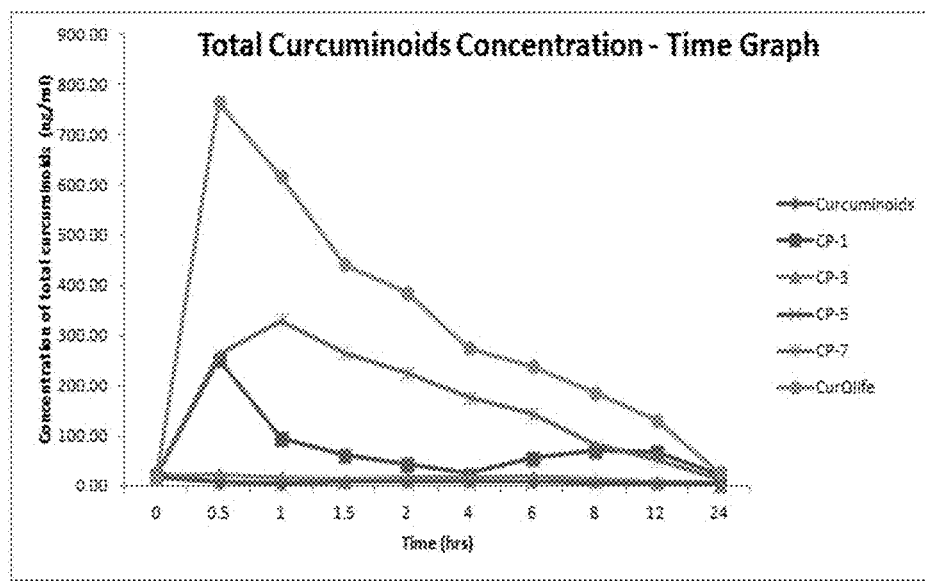
Fig. 6: CurQlife® Pharmacokinetics Graph in SD Rats
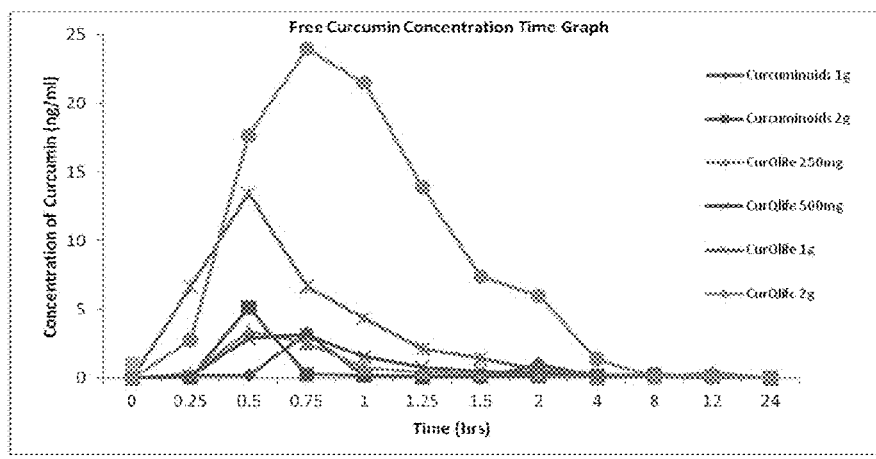
Fig. 7. Curcumin Concentration Time Graph for CurQlife and curcuminoids in Human Pharmacokinetic study

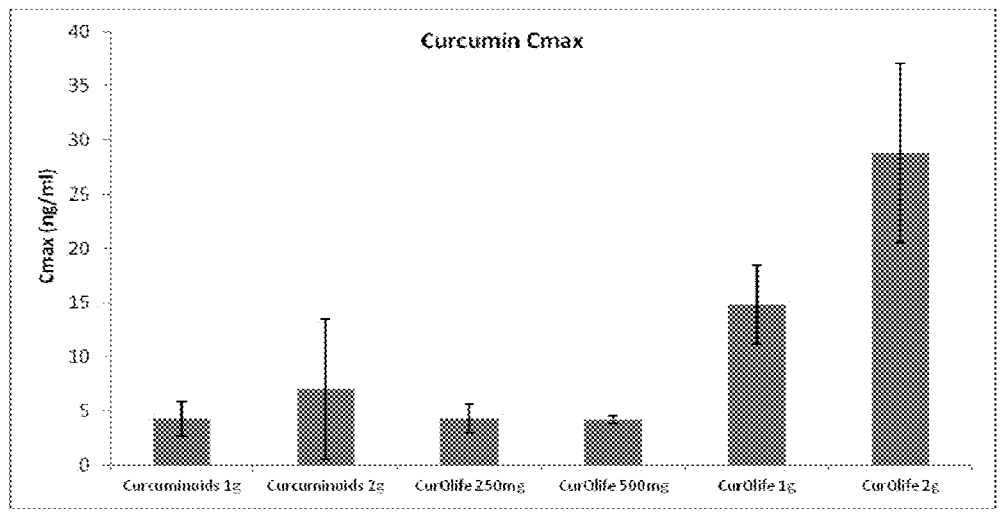
Fig. 8. Free Curcumin (C-I) Cmax for CurQlife in Human PK Study
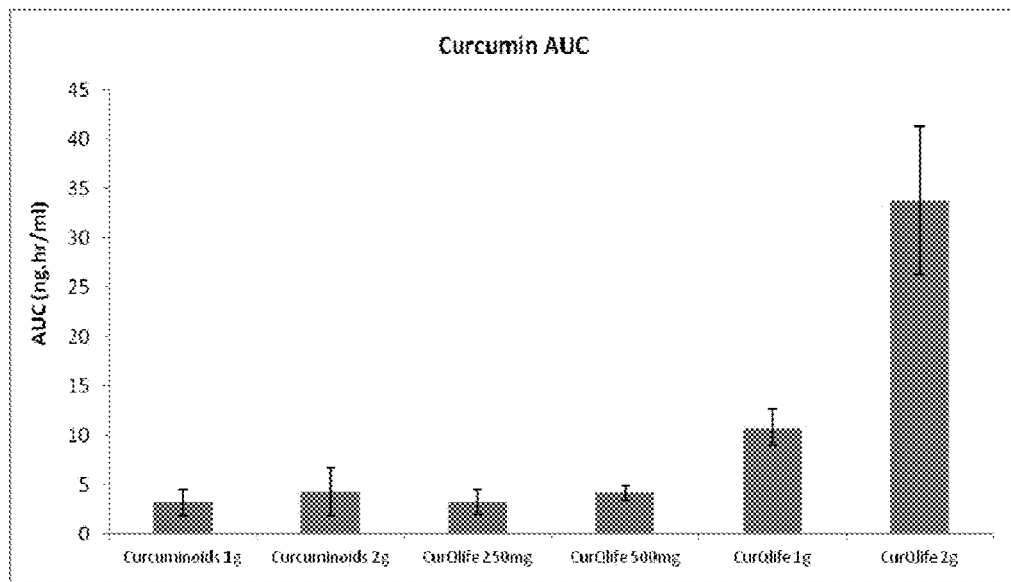
Fig. 9. Free Curcumin (C-I) $AUC_{0-24h}$ for CurQlife in Human PK Study

HIGHLY BIOAVAILABLE, WATER SOLUBLE AND SUSTAINED RELEASE NANOFORMULATIONS HYDROPHOBIC PLANT DERIVED COMPOUNDS AND EXTRACTS

CROSS-REFERENCE TO RELATED APPLICATIONS

This application is a continuation-in-part of parent International Application No. PCT/IN2013/000328, filed on May 21, 2013. The entire disclosure of the prior application is hereby incorporated by reference herein in its entirety.

TECHNICAL FIELD

The present disclosure relates to novel highly bioavailable, water soluble, sustained release nanoformulation(s) comprising unique proportion of the hydrophobic plant derived compound(s) in an emulsifier phase and aqueous phase to achieve the sustained release over a 24 hr time period and more.

The present disclosure is further directed towards formulating novel sustained release nanoformulation(s) containing unique proportion of the hydrophobic plant derived compound(s) in an emulsifier phase and aqueous phase to achieve ideal hydrophilic-lipophilic balance (HLB) for providing sustained release over a 24 hr time period and more.

The disclosure also relates to highly soluble, highly bioavailable and highly sustained release nanoformulations of plant derived hydrophobic compounds capable of delivering significantly higher amount of active molecules to the human and/or animal system more specifically to plasma and maintaining their concentration in the plasma for longer duration, thus rendering enhanced therapeutic efficacy with lower doses.

BACKGROUND

The biodiversity observed on the planet earth provides vast varieties of plants/trees which are explored over the centuries to understand their use in daily life both as source of food and medicine. The use of plants as a source of medicine came to limelight with Ayurveda which was developed between 2500 and 500 BC in India. India, a land known for tradition and herbal resource, recorded around 20,000 medicinal plants out of which only 35-40% are explored by the traditional communities.

Medicinal plants like Aswagandha, Amla, Brahmi, Guggul, Long pepper, Tulsi, Henna, Haridra, Neem and many more have been traditionally in use for treating various ailments via Ayurveda, Siddha, Unani and other traditional methods. The traditional medicinal system used these rich herbal sources either alone or in combination, together with other required ingredients to treat various conditions. Despite these uses of medicinal plants over the years there has been a lag to deliver a therapeutically efficacious drug/nutraceutical from a plant source. The traditional system of medicine had little scientific effort to validate these anecdotal uses that are traditionally known.

Despite the long historical use, little has been achieved in treating the diseases. The major problem associated with hydrophobic plant compounds and extracts is their poor bioavailability, leading to poor or decreased efficacy. The major hydrophobic compounds with poor bioavailability in plant extracts belong to phenolic compounds, flavonoids, stilbenes and lignans. Flavoniods may themselves be divided into 6 subclasses based on the type of heterocycle involved: flavonols, flavones, isoflavones, flavanones, anthocyanidins, and flavanols (catechins and proanthocyanidins). Most of the hydrophobic compounds like Curcuminoids, Boswellic acids, Resveratrol, Hypericin, Bacosides, Xanthorhizol, *Ginseng* extract, *Gingko biloba* extract and many others are proven to have several therapeutic benefits like anti-inflammatory, anti-oxidant, anti-obese, memory enhancing, anti-allergic, anti-microbial, anti-cancerous and many other medicinal activities. But, little has been achieved with respect to these molecules for the prevention and treatment of diseases due to their poor bioavailability and lack of sustained release in the body.

Many of the plant molecules as discussed above are hydrophobic in nature and hence are not water soluble. The poor bioavailability of these molecules reflects the lack of efficient natural drugs in the market, in spite of their traditionally known benefits. On the other hand, biopharmaceuticals have been suffering from instability and biological degradation before reaching the target site.

One of the best and thoroughly studied molecule that can be exemplified here is Curcumin. Curcumin and derivatives like Bisdemethoxycurcumin, Demethoxycurcumin, Bis-o-demethylcurcumin have been widely acknowledged as a botanical supplement with great potential to prevent and treat wide spectrum of therapeutic conditions. In addition, they have been proved to be remarkably safe in animal studies and in many clinical evaluations even at high doses (up to 12 g/day). However, the major problem limiting the commercial exploitation of their therapeutic effects is their low bioavailability and their fast elimination from the body, very often as quickly as in 30 mins.

The reasons for the poor bioavailability of curcuminoids may be attributed to poor absorption, high rate of metabolism and/or rapid elimination and clearance from the body. This is the same case with any of the hydrophobic plant molecules/extracts. Several studies failed to detect these compounds in the blood plasma/serum even after administration of high doses in animals and humans. Most of the phytochemicals such as curcumin and resveratrol show bioavailability of less than 1%. Curcumin when taken orally get metabolized to form curcumin glucoronide, curcumin sulphate, which are not biologically active and thus are eliminated from the system, which in turns leads to poor efficacy.

Many of the existing curcumin products in market are unformulated turmeric extract or formulated with suitable excipients to enhance the bioavailability. Some curcumin products use Phospholipids to enhance the bioavailability of curcumin. Other curcumin formulations contain piperine to enhance curcumin bioavailability.

The main issue to be addressed with the hydrophobic compounds is not only the bioavailability but also their availability in the systemic circulation for longer period (24 hours or more) in an biologically active form for sustained efficacy. An ideal formulation would be the one which can be retained in the body over a period of 12-24 hours and more, with significant amount of the active compound in the blood stream to provide the required therapeutic benefits. This could minimize the expenditure due to reduced dose and patient compliance of convenient dosing.

The time to reach maximum concentration ($T_{max}$), Maximum concentration ($C_{max}$), Area under the curve (AUC) and Half-life ($T_{1/2}$) are some of the important parameters to establish the systemic bioavailability of a particular drug/formulation. For a drug intended to provide sustained release and enhanced bioavailability, AUC should be higher with higher value for t½. Higher t½ indicates the longer stay of drug in the body and hence long lasting efficacy.

The product of above features will reduce the dose levels and also achieves enhanced bioavailability leading to enhanced therapeutic efficacy compared to existing products in market. The currently available phyto pharmaceutical compositions are way behind in providing a highly bioavailable and sustained release formulation, which is stable and water soluble.

Moreover the conventional methods and regular solubilization techniques are not efficient enough to solubilize high concentration of the plant molecules/extracts and also not successful in providing sustained release. Due to their lipophilic and hydrophobic nature, the choice of the right excipients, right combination of excipients and process of formulating such product is key to achieve the desired product.

Emulsifiers, which are classified under surfactants and also lipids, are widely used for solubilizing hydrophobic compounds and in formulating nanoemulsions.

Currently many curcuminoid products in market claim high bioavailability which are formulated using phospholipids or plant derived oils and so on. However, none of the prior arts discloses a nanoformulation containing unique proportion of the plant derived hydrophobic active compound(s) in an emulsifier phase and aqueous phase to achieve sustained release over a 24 hr time period and more.

Further, none of the prior art discloses the use of aqueous phase in combination with emulsifier phase to achieve a nanoemulsion with smaller particle size for sustained release and enhanced efficacy.

Hence, the present disclosure provides a unique proportion of the plant derived hydrophobic active compound(s) in an emulsifier phase and aqueous phase to provide enhanced efficacy and sustained release over a 24 hr time period and more.

Accordingly the present disclosure offers a potential successor in the field of drugs, biopharmaceuticals, nutritional/dietary supplements for human and/or animal application with a novel nanoemulsified composition with enhanced bioavailability and sustained release.

SUMMARY

The present disclosure provides novel sustained release nanoformulation(s)/delivery system having a unique proportion of the plant derived hydrophobic active compound(s)/extract(s) in an emulsifier phase and aqueous phase to achieve sustained release over a 24 hr time period or more.

In yet another aspect, the disclosure provides a water soluble nanoemulsified formulation(s) comprising one and/or combinations of plant derived hydrophobic active compound(s)/extract(s) in an emulsifier phase and aqueous phase to achieve enhanced and long lasting efficacy at low dose and low cost.

In yet another aspect, the disclosure provides a water soluble nanoemulsified formulation(s) comprising one and/or combinations of plant derived hydrophobic active compound(s)/extract(s) in an emulsifier phase and aqueous phase for protection from biological degradation.

In yet another aspect, the disclosure provides a water soluble nanoemulsified formulation(s) comprising one and/or combinations of plant derived hydrophobic active compound(s)/extract(s) in an emulsifier phase and aqueous phase for various therapeutic, preventative and general health supplement applications in animals and human beings.

In yet another aspect, the disclosure provides a water soluble nanoemulsified formulation(s) comprising one and/or combinations of plant derived hydrophobic active compound(s)/extract(s) in an emulsifier phase and aqueous phase for use as dietary supplements or nutraceuticals/health supplements/general supplements/OTC products.

In yet another aspect, the disclosure provides a water soluble nanoemulsified formulation(s) comprising one and/or combinations of plant derived hydrophobic active compound(s)/extract(s) in an emulsifier phase and aqueous phase either in liquid, semisolid or solid dosage form.

Various embodiments disclosed herein relate to a sustained release nanoformulation, comprising a dispersed phase in an amount of 60-95%, based on the weight of the formulation, and an aqueous phase. The dispersed phase comprises particles containing an emulsifier comprising a nonionic surfactant having an HLB value of 13 to 18; and a hydrophobic biologically active material in an amount of 0.0001 to 50%, based on the weight of the formulation. In various embodiments of the sustained release nanoformulation, the dispersed phase is present in an amount of 80-95%, based on the weight of the formulation; and the aqueous phase is present in an amount of 5-20%, based on the weight of the formulation.

In some embodiments, the particles in the dispersed phase have a mean particle size of less than about 250 nm, less than about 212 nm, or less than about 100 nm. In various embodiments, the dispersed phase comprises particles having a particle size range of between 69 nm and 212 nm; a mean particle size of about 100 nm; or both a mean particle size of about 100 nm and a particle size range of between 69 nm and 212 nm. In various embodiments, between 75% and 90% of the hydrophobic biologically active material is released from the nanoformulation when the nanoformulation is added to water. The nanoformulation allows sustained release of the hydrophobic biologically active material over a period of at least 24 hours.

In various embodiments disclosed herein, the sustained release nanoformulation contains a hydrophobic biologically active material which is a natural product, a synthetically derived product, or a mixture thereof. The hydrophobic biologically active material may be an extract or phytochemical obtained from at least one plant selected from the group consisting of *Curcuma longa, Ginseng, Ginkgo biloba, Garcinia mangostana, Ocimum basilicum, Zingiber officinale, Tribulus terrestris, Sphaeranthus indices, Annona Squamosa, Moringa oleifera, Murraya koenigii,* and mixtures thereof. The hydrophobic biologically active material may be a compound selected from the group consisting of at least one curcuminoid selected from the group consisting of curcumin, demethoxycurcumin, bisdemethoxycurcumin, and bis-o-demethyl curcumin; at least one boswellic acid compound; Resveratrol; Hypericin; Bacoside(s); Xanthorhizol; Luteolin; Pyrogallol; Genistein; Wogonin; Morin; Kaempferol; and mixtures thereof.

In various embodiments disclosed herein, the sustained release nanoformulation contains a dispersed phase comprising particles containing a nonionic surfactant selected from the group consisting of Polysorbates, Polyethylene glycols, Polyethylene glycol esters, Glycerol esters, and mixtures thereof.

Some embodiments disclosed herein relate to free flowing solid powders prepared from the sustained release nanoformulation. The powders may be prepared by subjecting the nanoformulation to encapsulation, nanospray drying, thin layer drying, or freeze drying; or by combining the nanoformulation with a carrier selected from the group consisting of microcrystalline cellulose, precipitated silica, anhydrous calcium phosphate dibasic, mannitol, hydroxypropyl methylcellulose, cellulose, and mixtures thereof.

Other embodiments disclosed herein relate to liquid neutraceutical compositions, prepared by dispersing the nanoformulation in an aqueous medium. Further embodiments relate to gels or creams, prepared by combining the nanoformulation with a wax or polymer. Suitable waxes or polymers include hydroxypropyl methylcellulose, isopropyl myristate, collagen, cetyl alcohol, metal salts of stearic acid, and carbopol.

Various embodiments described herein relate to a process for formulating a sustained release nanoformulation of a hydrophobic biologically active material, by:
 a) preheating an emulsifier comprising a nonionic surfactant having an HLB value of 13 to 18 to a temperature below the melting point of the hydrophobic biologically active material;
 b) adding the hydrophobic biologically active material to the preheated emulsifier and solubilizing the hydrophobic biologically active material in the emulsifier to form a mixture;
 c) cooling the mixture to room temperature; and
 d) adding a desired quantity of an aqueous phase, followed by mixing, to obtain a nanoemulsified formulation of hydrophobic active comprising particles having a particle size of between about 69 nm and about 212 nm.

The step of solubilizing the hydrophobic biologically active material in the emulsifier may be done by:
 heating the mixture at a temperature in the range of 50-200° C. to obtain solubilization of the hydrophobic biologically active material in the emulsifier;
 sonicating the mixture to obtain solubilization of the hydrophobic biologically active material in the emulsifier;
 vortexing the mixture to obtain solubilization of the hydrophobic biologically active material in the emulsifier; or
 ultra-high pressure homogenization of the mixture to obtain solubilization of the hydrophobic biologically active material in the emulsifier.

Various embodiments relate to treatment of disease conditions selected from the group consisting of inflammation, osteoarthritis, allergy, obesity, neuro degenerative disorder(s), diabetes, cancer, cardiovascular disorder(s) and microbial disorder(s) by administering the sustained release nanoformulations disclosed herein to a subject in need thereof.

BRIEF DESCRIPTION OF THE DRAWINGS

FIG. 1: Malvern Particle Size analysis of CurQlife®.

FIG. 2: Morphological Characterization of CurQlife® by Scanning Electron Microscopy (SEM).

FIG. 3: Confocal Microscopy of CurQlife®

FIG. 4: Preliminary dissolution study (pH-1.2) results of CurQlife® in comparison with other curcuminoid products in the market.

FIG. 5: Preliminary dissolution study (pH-6.8) results of CurQlife® in comparison with other curcuminoid products in the market.

FIG. 6: CurQlife® Pharmacokinetics Graph in SD Rats

FIG. 7: Curcumin Concentration Time Graph for CurQlife® and curcuminoids in Human Pharmacokinetic study FIG. 8: Free Curcumin (C-I) $C_{max}$ for CurQlife® in Human PK Study FIG. 9: Free Curcumin (C-I) $AUC_{0-24h}$ for CurQlife® in Human PK Study

DETAILED DESCRIPTION

The subject matter will now be described in detail in connection with certain embodiments, so that various aspects thereof may be fully understood and appreciated.

In various embodiments, the disclosure describes nanoformulation(s)/delivery composition having a unique proportion of the plant derived hydrophobic active compounds(s), emulsifier phase and aqueous phase to achieve sustained release over a 24 hr time period and more.

The plant derived hydrophobic compound(s) as disclosed can be either purified molecule(s) or extract(s).

In yet another embodiment, the use of the compound(s) either alone or in combination thereof is disclosed.

The present disclosure is directed to nanoformulation(s) and method of producing such nanoformulation to improve the bioavailability with sustained release for use in humans and/or animals as drug and/or dietary/nutritional supplement/OTC products/health supplements/Ayurvedic (botanical) medicine.

The novel nanoformulations and the process of producing the same enables to attain unique nano size which allows to cross the required biological barriers to provide higher amount of active ingredient for higher beneficial effect. The essential biological barriers might include, gut mucosa, buccal lining, nasal mucosa, cell membranes, blood brain barrier, skin, respiratory and urinary and anal lining.

The disclosure further relates to nanoformulations of plant derived hydrophobic compounds with poor bioavailability.

The disclosure relates to hydrophobic plant molecules/extracts which are selected from but not restricted to phenolic acids, flavonoids, stilbenes, and lignans. Flavonoids may be isoflavones, flavanones, anthocyanidins, and flavanols (catechins and proanthocyanidins).

The plant molecules/extracts are selected from but not restricted to *Curcuma longa* extract, Curcumin, Demethoxycurcumin, Bisdemethoxycurcumin, Bis-o-demethylcurcumin, and derivative of curcumin, *Boswellia Serrata* extract, Boswellic acids, Beta boswellic acid, keto beta boswellic acid, acetyl keto beta boswellic acid, Resveratrol, Hypericin, *Bacopa monneri* extract, Bacoside A, Bacoside A3, Bacoside B, Xanthorhizol, *Ginseng* extract, Genistein, *Gingko biloba*, Coenzyme Q10, Pycnogenol, Luteolin, Kaempferol, Capsaicin, *Rubia cordifolia* extract, Lycopene, Pyrogallol, Lutein, *Lawsennia iermis* extract, *Aloe vera* extract, Beta carotene, Piperine and any other hydrophobic plant molecules/extracts.

The plant derived hydrophobic compound(s) described above can be obtained either naturally and/or by synthetic and/or semi synthetic process.

In yet another embodiment, the disclosure is directed to nanoformulations of hydrophobic compound(s) having anti-inflammatory, anti-allergic, anti-oxidant, memory enhancing, anti-obese, neuro protective, anti-diabetic, anti-cancerous, cardio protective, eye protective and anti-microbial activity.

In yet another aspect disclosed herein, the said hydrophobic plant molecules/extracts, can be used either alone or in combination to formulate into nanoemulsion(s)/nanoformulation(s) giving rise to the oral, nasal, anal, topical, vaginal, ocular, buccal dosage forms. The disclosure further relates to nanoformulations of the hydrophobic compounds using unique process to achieve water soluble, bioavailable and sustained release formulation(s).

In another embodiment, the disclosure describes the method of obtaining such nanoformulations.

As used herein the term emulsifier(s) enhance the solubility of hydrophobic/lipophilic compounds/extracts.

The use of emulsifier(s) for solubilizing the hydrophobic compounds is well known in the prior art. However, the present disclosure describes a unique proportion of the hydrophobic active compound(s), emulsifier phase and aqueous phase, which is the main principal in solubilizing higher concentrations of such hydrophobic compounds with higher bioavailability and sustained release.

The concentration of the emulsifier phase in the nanoformulations ranges from 60 to 95% and more preferably 80%.

Further, the disclosure relates to sustained release nanoformulation(s) with unique hydrophilic lipophilic balance (HLB), to achieve nanoparticle of smaller size for enhanced efficacy.

In yet another aspect, the disclosure describes the use of emulsifiers(s) which are anionic, cationic or non-ionic selected from but not limited to Polysorbates preferably Polysorbate 80 and Polysorbate 20, Polyethylene glycols preferably Polyethylene glycol 200 and Polyethylene glycol 400, Polyethylene glycol esters and Glycerol esters.

For the purpose of the present disclosure, the emulsifier(s) can be used alone or in combination to maintain the total HLB of the nanoformulation between 13-18.

The present disclosure further relates to preparing the nanoemulsion(s) with unique particle size, which enhance the bioavailability of the said hydrophobic compounds and also to provide sustained release of the same over a 24 hour time period. The prior art teaching does not provide a method or a product to develop such nanoformulations, with enhanced bioavailability and sustained release.

The higher the HLB value the more water soluble or hydrophilic the emulsifiers are. Hence, it is important that the nano formulations developed ideally comprise emulsifier(s) with a HLB value ranging from 13-18 to achieve enhanced bioavailability and sustained release. It was found that nanoformulations with emulsifier phase HLB below 13 or above 18 could not achieve sustained release bioavailable formulations.

The concentration of the aqueous phase in the nanoformulations ranges from 5 to 20% and more preferably 5-10%.

In yet another embodiment, the disclosure provides a process to solubilize hydrophobic compounds with the help of energy in the form of sonication, heating, vortexing, shaking or any other forms of energy.

According to the inventive process, the emulsifier phase is preheated to a temperature below melting point of the hydrophobic active followed by addition of desired concentration of hydrophobic compound(s) to the emulsifier phase. The mixture is subjected to sonication/heating/vortexing/shaking to solubilize the hydrophobic compound(s). Upon solubilization, distilled water of desired concentration is added to the mixture to form nanoformulation(s). For the purpose of solubilization, heating is more preferable as it is quick and effective process. Heating the mixture of hydrophobic compounds and surfactants for a period of 2-3 hours and preferably between 30-60 mins at a temperature ranging between 50-200° C. and preferably between 100-140° C. and subsequent adding distilled water upon cooling to room temperature.

The hydrophobic plant compound(s)/extract(s) can be solubilized between 0.0001-50% using the method of the present disclosure and more preferably between 12-20%.

The nanoformulation(s) of the present disclosure entraps the active compound within the spherical droplets which are in nanometer range. This entrapment offers bioprotection for the active compound(s) from hydrolytic and/or enzymatic degradation.

Solubilizing the hydrophobic compounds using surfactants with the aid of heat energy disperses the hydrophobic compounds from the larger crystal lattice into individual molecules there by reducing the particle size leading to complete solubilization upon heating. Hence, the nanoformulations are completely soluble in water, which no other existing products could achieve.

In yet another embodiment, the present disclosure discloses nanoformulations in a free flowing solid powder form, which is obtained by subjecting the liquid nanoformulations to techniques not limited to encapsulation, nanospray drying, thin layer drying, freeze drying, using carriers like Microcrystalline cellulose, Precipitated Silica, Fujicalin, Nucelin, Mannitol, Hydroxypropyl Methylcellulose, Arbocel, Silica derivatives.

In yet another embodiment, the present disclosure discloses nanoformulations in a semi solid gel, lotion or cream form, which is obtained by formulating the liquid formulation with suitable polymers not limited to Hydroxypropyl Methylcellulose, Isopropyl myristate, Collagen, Glycerol, Cetyl alcohol, Sterates of magnesium, Zinc, Calcium and Carbopol.

In yet another embodiment, the disclosure is directed to nanoformulations of hydrophobic compounds/extracts with enhanced bioavailability and sustained release over a period of 24 hours compared to any existing products. The nanoformulations of the present disclosure further are effective in delivering high concentrations of the active compound which was not disclosed in any of the known prior art. For the said reasons, the nanoformulations of the present disclosure are far superior to any of the existing products in terms of bioavailability, sustained release profile, low dose and low cost.

In yet another embodiment, the disclosure is directed to nanoformulations of hydrophobic compound(s) as drugs, dietary/nutritional supplement for use in humans and animals.

In yet another embodiment, the disclosure is directed to nanoformulations of hydrophobic compound(s) for the treatment and/or prevention of inflammation, osteoarthritis, allergy, obesity, neuro degenerative disorders, diabetes, cancer, cardio vascular disorders and microbial disorders.

In yet another embodiment, the disclosure is directed to nanoformulations of hydrophobic compound(s) which can be administered as pharmaceuticals/nutraceuticals/ayurvedic/dietical compositions to the subject in need thereof.

Various formulations were developed using one or combination of hydrophobic compound(s) along with single or combination of surfactants which are exemplified herein. Having described the disclosed subject matter with reference to certain embodiments, other embodiments will become apparent to one skilled in the art from consideration of the specification.

The subject matter is further described by reference to the following examples. It will be apparent to those skilled in the art that many modifications, both to materials and methods, may be practiced without departing from the scope of the subject matter disclosed herein.

Example 1: Process of Preparing 15% Curcuminoids Formulation a) 15 gms of accurately weighed Curcuminoids was used for obtaining nano formulation.

b) Surfactants (12 g) Tween 80, (6 g) Tween 20 and (62 g) PEG 400 were accurately weighed and heated to 120° C.
c) To the preheated surfactants, curcuminoids (15 g) was added and stirred continuously till the curcuminoids are completely dissolved.
d) Once the curcuminoids are completely solubilized, it's cooled to room temperature and distilled water (5 g) is added and stirred well to obtain a nanoemulsified formulation.

Example 2: Process of Preparing 10% Curcuminoids Formulation (CurQlife®)

a) 10 gms of accurately weighed Curcuminoids was used for obtaining the nanoformulation.
b) Surfactants (PEG 200 (13 g), Tween 20 (67 g)) were accurately weighed and heated to 120° C.
c) To the preheated surfactants, curcuminoids (10 g) was added and stirred continuously till the curcuminoids are completely dissolved.
d) Once the curcuminoids are completely solubilized, it's cooled to room temperature and distilled water (10 g) is added and stirred well to obtain a nanoemulsified formulation.

Example 3: Process of Preparing 15% Bis-o-Demethyl Curcumin (BDMC) Formulation a) 15 gms of accurately weighed BDMC was used for obtaining nano formulation.
b) Surfactants (PEG 200 (13 g), Tween 20 (67 g)) were accurately weighed and heated to 120° C.
c) To the preheated surfactants, BDMC (15 g) was added and stirred continuously till the BDMC is completely dissolved.
d) Once the BDMC is completely solubilized, it's cooled to room temperature and distilled water (5 g) is added and stirred well to obtain a nanoemulsified formulation.

Example 4: Composition of Nanoformulations of Hydrophobic Compounds

Example 5: Particle Size Analysis of CurQlife

Dynamic Light Scattering (sometimes referred to as Photon Correlation Spectroscopy or Quasi-Elastic Light Scattering) is a technique for measuring the size of particles typically in the sub micron region. DLS measures Brownian motion and relates this to the size of the particles. The scattered light is then detected by the detector and translated to an auto-correlator. Freshly prepared sample was transferred to Cuvette and the sample was analysed in 90 PLUS Particle Size Analyzer (Brookhaven Instrument Corporation) under the below mentioned conditions.

| Parameters | Value |
| --- | --- |
| Angle of diffraction | 90° |
| Temperature | 25° C. |
| No of cycles | 5 |
| Time duration | 1 min for each cycle |

The mean particle size of CurQlife (10%) was found to be 102.6 nm, upon diluting the CurQlife sample with water in the ratio of 1:1000. The particle size in CurQlife in this dilution ranges from ~81-181 nm as depicted in FIG. 1.

Example 6: Morphological Characterization of CurQlife by Scanning Electron Microscopy (SEM)

SEM allows visualization and characterization of particles by providing better information on its structure, shape and distribution. SEM is an important technique for measuring the size of particles typically in the sub-micron region. In SEM, primary beam of electron scans the surface of the sample and then the secondary electrons generated from the sample are detected by the detectors to analyze the surface morphology of sample.

Freshly prepared and diluted sample was air dried on the glass slide and the sample was analyzed using FEI Quanta 400 FEG, as it has got better magnification and extended low-vacuum capabilities for the really challenging samples and less surface charging of the sample as compared to Quanta 200 FEI. The image was taken on the 500 nm scale bar and at the magnification of 60,000×.

| Sl. No | Hydrophobic Compound | Emulsifier Phase | | | | | Hydrophobic Active | Aqueous Phase |
| --- | --- | --- | --- | --- | --- | --- | --- | --- |
| | | PEG200 | PEG400 | Tween 20 | Tween 80 | Acconon | | |
| 1 | Resveratrol | 0 | 1.6 | 11.8 | 0.6 | 0 | 2 | 4 |
| 2 | Curcumin | 0 | 2.4 | 12.4 | 1.2 | 0 | 2 | 2 |
| 3 | Hypercine | 0 | 1.4 | 0 | 13.6 | 0 | 2 | 3 |
| 4 | Bis-o-demethyl curcumin | 0 | 2 | 0 | 14 | 0 | 2 | 2 |
| 5 | Boswellic Acid | 2 | 0 | 13 | 0 | 0 | 2 | 3 |
| 6 | Curcuminoids (95% extract) (CurQlife) ® | 2.6 | 0 | 13.4 | 0 | 0 | 2 | 2 |
| 7 | Bacoside A | 0 | 0 | 11.4 | 0 | 3.6 | 2 | 3 |
| 8 | Curcuminoids | 0.91 | 3.77 | 9.32 | 0 | 0 | 5 | 1 |
| 9 | Xanthorhizol | 0 | 0 | 10 | 0 | 6 | 2 | 2 |
| 10 | Luteolin | 0 | 0 | 11 | 0 | 3 | 2 | 4 |
| 11 | Pyrogallol | 0.4 | 1 | 9.6 | 3 | 0 | 2 | 4 |
| 12 | Kaempferol | 0.6 | 1.8 | 3 | 9.6 | 0 | 2 | 3 |
| 13 | Emodin | 0.8 | 2.6 | 3 | 9.6 | 0 | 2 | 2 |
| 14 | Genistein | 0 | 2 | 0 | 14 | 0 | 2 | 2 |
| 15 | Ellagic Acid | 2 | 0 | 13 | 0 | 0 | 2 | 3 |
| 16 | Psolaren | 2.6 | 0 | 13.4 | 0 | 0 | 2 | 2 |
| 17 | Catechin | 0 | 0 | 11.4 | 0 | 3.6 | 2 | 3 |

| Parameters | Value |
| --- | --- |
| Voltage | 30 KV. |
| Temperature | 25° C. |
| Magnification | 60 000x |
| Time duration | Half an hour |
| Scale bar | 500 nm |

SEM results show clearly spherical shaped particles. SEM image shows particles of more or less evenly sized particles distributed evenly throughout the test sample tested (FIG. 2). These particles are found to be in nano-meter range. Majority of the particles are less than 100 nm size and few are found to be around 100 nm range.

Example 7: Morphological Characterization of CurQlife (10%) Using Confocal Microscopy Confocal microscopy allows visualization and characterization of structures on the surface and also inside the particles, provided that the material is sufficiently transparent and fluorescent or fluorescent labeled. Curcuminoids loaded particles can be visualized by using confocal microscope, since Curcumin is naturally fluorescent in the visible green spectrum, no further labeling of Curcumin will be needed.

0.1 ng/ml concentration of CurQlife product in water was used for the study. Diluted sample was filtered using 0.45μ Sartorius filter. 2-3 drops of sample was placed on the slide and was observed under the Confocal microscope.

Freshly prepared sample was transferred to the slide and was analyzed by using LSM (Laser Scanning Microscope) 710, under dark condition.

| Model name | LSM 710 Laser Scanning Microscope |
| --- | --- |
| Company | Carl Ziess, Germany |
| Objective | Plan-ApoChromat 40X 0.95 Korr M27 |
| Laser | Argon 488 |
| Laser Power | 2% |
| Filter | 493-638 |

Spherical green fluorescence was observed under the confocal microscope including the presence of curcuminoids. Working test sample with 0.1 ng/ml concentration of CurQlife product in water, showed clear individual particles with green fluorescence. These particles were found to be in proper spherical shape of different sizes. Almost all the particles were found to have regular spherical shaped structure (FIG. 3a-d).

Example 8: Solubility Studies

Solubility of curcuminoids in water is an important quality which all the bioavailable curcuminoids formulation is expected to possess. Hence, CurQlife® was compared with different bioavailable curcuminoid products available in the market to test their solubility in water.

Solubility studies were carried out in comparison with marketed products by dissolving respective products in the concentration of 1 mg/ml of water. Vortexed for 5 minutes filtered using 0.2μ filter paper and the filtrate was tested for curcuminoid content using HPLC. Results of HPLC analysis for Curcuminoids are shown in Table. 1 Below is the list of marketed curcuminoid products tested;

Meriva (CP-1)—Batch No FG-9212
C3 Complex (CP-2)—Batch No 1103071
C3 Complex+Bioperine (CP-3)—Batch No 2011001-A

TABLE 1

Results of consolidated solubility study of CurQlife ® in comparison with other bioavailable curcuminoids product in market

| Sl. No. | Product | % of Total Curcuminoids in Product | Theoretical/ expected concentration of curcuminoid in water | Actual concentration of curcuminoid present in water | % Recovery/ Solubility of curcuminoids |
| --- | --- | --- | --- | --- | --- |
| 1. | CurQlife ® | 9.4 | 9.4 mg | 8.1 mg | 86.30 |
| 2. | CP-1 | 16.68 | 16.68 mg | ND | 0 |
| 3. | CP-2 | 85.8 | 85.8 mg | ND | 0 |
| 4. | CP-3 | 90.04 | 90.04 mg | ND | 0 |

CP—Curcuminoid Product in market

Result (Table 1) showed that among all the bioavailable products tested, CurQlife® showed high solubility and the percentage solubility or recovery of curcuminoids in water. CurQlife® was found to be superior in terms of solubility in water compared to all other products. Interestingly none of the other bioavailable curcuminoid products were soluble in water in the concentration (1 mg/ml) tested.

Example 9: Analysis of Nature of Curcuminoid in Water

It is important to retain the structure, chemical and biological properties of curcuminoids after dissolution in water so as to retain its biological activity. To evaluate the change in the structure, chemical properties and biological properties, curcuminoids products were dissolved in water, filtered and filtrates were tested for the change in λmax using spectrophotometer.

Interestingly except for CurQlife®, there is significant change in λmax value for other marketed bioavailable curcuminoid products (Table 2). This may be due to complexation of curcuminoids with other excipients during formulation or might be due to degradation of curcuminoids in water. This clearly infers that CurQlife® doesn't change the nature of Curcuminoids and hence indicates the higher therapeutic activity. Below is the list of marketed curcuminoid products tested;

Meriva (CP-1)—Batch No FG-9212
C3 Complex (CP-2)—Batch No 1103071
C3 Complex+Bioperine (CP-3)—Batch No 2011001-A

TABLE 2

λmax of curcuminoids from different bioavailable curcuminoid formulations in water.

| Sl. No. | Product | λmax (nm) | Absorbance (OD) at λmax |
|---|---|---|---|
| 1. | CurQlife | 422 | 0.566 |
| 2. | CP-1 | ND | ND |
| 3. | CP-2 | 339 | 0.241 |
| 4. | CP-3 | 330 | 0.137 |

ND—Not detected.
CP—Curcuminoid Product in market

Example 10: Dissolution Study of CurQlife®

In order to assess the bioequivalence and to predict the bioavailability of CurQlife® in comparison to other bioavailable curcuminoid products in market, dissolution study was carried out. Dissolution study is a standard method for measuring the rate of drug release from dosage form. The preliminary dissolution study results, described in FIG. 4 and FIG. 5 at different pH of 1.2 and 6.8, reflecting stomach and intestine environment respectively, confirms that CurQlife® possess far superior dissolution properties compared to all other marketed products. Hence based on the dissolution study results, CurQlife® is expected to have much better bioavailability and pharmacokinetic properties than other products in the market.

Two of the dissolution bowls were filled with 500 mL of dissolution medium each. One bowl with 500 mL dissolution medium serves as blank. The dissolution apparatus was programmed so that the temperature was 37° C. and paddle rotation of 100 rpm. After the temperature in the bowls reached 37° C., 500 mg of test substance was added to one dissolution bowl. Samples of 5 mL were withdrawn at time intervals of 0, 10, 20, 30, 40, 50, 60, 120, 300, 600, 900, 1800, 2700, 3600 sec. The samples were centrifuged at 2000 rpm to facilitate easy filtration through 0.22 micron syringe filters. Centrifuged samples were filtered using 0.22 micron filters to remove finely suspended particles. Filtered samples were analyzed by HPLC to determine % release with time. A graph with time versus % release was plotted (FIG. 4 and FIG. 5)

Below is the list of marketed curcuminoid products tested in the dissolution study;
Meriva (CP-1)—Batch No FG-9212
C3 Complex (CP-2)—Batch No 1103071
C3 Complex+Bioperine (CP-3)—Batch No 2011001-A
Vivomeric (CP-4)
BCM-95 (CP-5)—Batch No 66250
Longvida (CP-6)—Batch No 44375
Theracurmin (CP-7)—Batch No 0120-957-145

Example 11: Oral Bioavailability Study of CurQlife® in SD Rats

Pharmacokinetics (PK) is a fundamental scientific discipline that underpins applied therapeutics. Drugs with poor PK are reported to be poorly absorbed into the biological system and hence are therapeutically inefficient. Current study was conducted to evaluate the bioavailability of orally administered CurQlife® and marketed curcuminoid products in Sprague Dawley rats. Total of 36 animals were divided into 6 groups having six numbers of animals in each group. The test substances were administered orally to the animals once on Day −1 at 500 mg/Kg body weight dose equivalent to Active ingredient. Control or 0th time blood samples were collected from all the animals before dosing the test substance, followed by blood sampling at 0.5, 1, 1.5, 2, 4, 6, 8, 12 and 24 hrs after dosing the test substance by sinus orbital plexus under anaesthesia. Serum was separated from blood by centrifugation. Serum was acidified with Concentrated HCl and was extracted with methanol and centrifuged to collect the supernatant. The supernatant was subjected to LC-MS/MS analysis for estimation of curcumin concentration in serum samples.

Below is the list of marketed curcuminoid products tested in the study;
Meriva (CP-1)—Batch No FG-6558
C3 Complex+Bioperine (CP-3)—Batch No 2011001-A
BCM-95 (CP-5)—Batch No 66250
Theracurmin (CP-7)—Batch No 0120-957-145

The results obtained confirmed superior bioavailability of CurQlife® compared to unformulated curcuminoids and other marketed products. CurQlife® was found to be 20 fold more bioavailable compared to unformulated curcuminoids and 3.8 fold more compared to closest marketed product (CP-1).

The summary of PK results is tabulated in Table 3. CurQlife® provided sustained release compared to other products and also delivers higher amount of curcuminoids over a period of 24 hrs (FIG. 6). The study confirmed the superior bioavailability of CurQlife®, which can be correlated to its enhanced efficacy.

TABLE 3

Pharmacokinetic parameters of CurQlife ® and other marketed products

| Products | $AUC_{0-t}$ | Cmax |
|---|---|---|
| Curcuminoids | 173 ± 38 | 31 ± 3 |
| CP-1 | 1111 ± 239 | 257 ± 16 |
| CP-3 | 238 ± 15 | 40 ± 9 |
| CP-5 | 113 ± 7 | 20 ± 3 |
| CP-7 | 2319 ± 376 | 330 ± 40 |
| CurQlife ® | 3570 ± 499 | 828 ± 108 |

CP—Curcuminoid Product in market

Example 12: Human Pharmacokinetic Study of CurQlife®

A clinical study was conducted to determine the bioavailability of different doses of CurQlife in healthy, adult, human, subjects under fasting conditions. Different formulations used in this study are CurQlife 250 mg, CurQlife 500 mg, CurQlife 1 g, CurQlife 2 g, Curcuminoids 1 g and Curcuminoids 2 g. The bioavailability of Curcumin in blood was estimated at periodical intervals over a period of 24 hours, 0.00 (predose), 0.25, 0.50, 0.75, 1.00, 1.25, 1.50, 2.00, 4.00, 8.00, 12.00 and 24.00 hours (post-dose). The Pharmacokinetic parameters assessed were Cmax, Tmax, t ½, $AUC_{0-t}$, $AUC_{0-inf}$. A total of 24 subjects, after fulfilling inclusion and exclusion criteria (4 subjects in each group×6 groups) were screened and enrolled in the study as per the randomization number. Curcumin plasma concentrations were estimated in the samples using LCMS-MS. All the formulations were well tolerated in the subjects. The Bioavailability results confirmed that the pharmacokinetic parameters like Cmax, T max, t ½, $AUC_{0-t}$, $AUC_{0-inf}$ of Curcumin, were superior in CurQlife dosed subjects as compared to unformulated curcuminoids. (FIG. 7). AUC and Cmax graphs of CurQlife are depicted in FIGS. 8 & 9.

Curcumin bioavailability in CurQlife treated group is 48-fold higher (on a per mg basis) than unformulated curcumin.

We claim:

1. A sustained release nanoformulation, comprising:
an emulsifier component in an amount of 60-95%, based on the weight of the formulation, said emulsifier component consisting of both i) a polysorbate and ii) a polyethylene glycol having a molecular weight of about 200 to about 400 or an ester of said polyethylene glycol; and
particles of a hydrophobic biologically active material in an amount of 0.0001 to 50%, based on the weight of the formulation; and
an aqueous component;
wherein between 75 to 90% of the hydrophobic biologically active material is released from the nanoformulation when the nanoformulation is added to water; and
said particles have a particle size of less than about 250 nm upon dilution with water;
wherein the hydrophobic biologically active material is a natural product, a synthetically derived product, or a mixture thereof.

2. The sustained release nanoformulation according to claim 1, wherein said particles have a mean particle size of less than about 100 nm upon dilution with water.

3. The sustained release nanoformulation according to claim 1, wherein:
said particles have a particle size range of between 69 nm and 212 nm upon dilution with water;
said particles have a mean particle size of about 100 nm upon dilution with water; or
said particles have a mean particle size of about 100 nm and a particle size range of between 69 nm and 212 nm upon dilution with water.

4. The sustained release nanoformulation according to claim 1, wherein:
the emulsifier component is present in an amount of 80-95%, based on the weight of the formulation; and
the aqueous component is present in an amount of 5-20%, based on the weight of the formulation.

5. The sustained release nanoformulation according to claim 1, wherein the nanoformulation allows sustained release of the hydrophobic biologically active material over a period of at least 24 hours.

6. The sustained release nanoformulation according to claim 1, wherein the hydrophobic biologically active material is selected from the group consisting of:
at least one curcuminoid selected from the group consisting of curcumin, demethoxycurcumin, bisdemethoxycurcumin, and bis-o-demethyl curcumin; at least one boswellic acid compound; Resveratrol; Hypericin; Bacoside(s); Xanthorhizol; Luteolin; Pyrogallol; Genistein; Wogonin; Morin; Kaempferol; and mixtures thereof.

7. The sustained release nanoformulation according to claim 1, wherein the hydrophobic biologically active material is an extract or phytochemical obtained from at least one plant selected from the group consisting of *Curcuma longa*, *Ginseng*, *Ginkgo biloba*, *Garcinia mangostana*, *Ocimum basilicum*, *Zingiber officinale*, *Tribulus terrestris*, *Sphaeranthus indicus*, *Annona Squamosa*, *Moringa oleifera*, *Murraya koenigii*, and mixtures thereof.

8. A free flowing solid powder, prepared by subjecting the sustained release nanoformulation according to claim 1 to encapsulation, nanospray drying, thin layer drying, or freeze drying.

9. A free flowing solid powder, prepared by combining the sustained release nanoformulation according to claim 1 with a carrier selected from the group consisting of microcrystalline cellulose, precipitated silica, anhydrous calcium phosphate dibasic, mannitol, hydroxypropyl methylcellulose, cellulose, and mixtures thereof.

10. A liquid nutraceutical composition, prepared by dispersing the sustained release nanoformulation according to claim 1 in an aqueous medium.

11. A composition in the form of a gel or cream, comprising the sustained release nanoformulation according to claim 1 and a wax or polymer;
said wax or polymer being selected from the group consisting of hydroxypropyl methylcellulose, isopropyl myristate, collagen, cetyl alcohol, metal salts of stearic acid, and carbopol.

12. The sustained release nanoformulation according to claim 1, wherein the emulsifier component consists of i) a single polysorbate and ii) a single polyethylene glycol having a molecular weight of about 200 to about 400.

13. The sustained release nanoformulation according to claim 1, wherein the polysorbate is a mixture of two polysorbates.

14. The sustained release nanoformulation according to claim 1, wherein the polyethylene glycol having a molecular weight of about 200 to about 400 is a mixture of two polyethylene glycols.

15. A sustained release nanoformulation, comprising:
an emulsifier component in an amount of 60-95%, based on the weight of the formulation, said emulsifier component comprising:
a. an emulsifier consisting of a mixture of a polysorbate and a polyethylene glycol having a molecular weight of about 200 to about 400; and
b. particles of a hydrophobic biologically active material in an amount of 0.0001 to 50%, based on the weight of the formulation; and
an aqueous component;
wherein between 75 to 90% of the hydrophobic biologically active material is released from the nanoformulation when the nanoformulation is added to water; and
said particles have a particle size of less than about 250 nm upon dilution with water;
wherein the hydrophobic biologically active material is a natural product, a synthetically derived product, or a mixture thereof.

16. The sustained release nanoformulation according to claim 15, wherein the nonionic surfactant consists of a mixture of a polysorbate and a polyethylene glycol;
wherein the mixture contains between 16.25% and 77.5% polyethylene glycol, based on the weight of the mixture.

17. A process for formulating the sustained release nanoformulation of claim 1, said process comprising:
(a) preheating the emulsifier component consisting of both i) a polysorbate and ii) a polyethylene glycol having a molecular weight of about 200 to about 400 or an ester of said polyethylene glycol, wherein said emulsifier component has an HLB value of 13 to 18;
(b) adding the hydrophobic biologically active material to the preheated emulsifier component and solubilizing the hydrophobic biologically active material in the emulsifier component to form a mixture;
(c) cooling the mixture to room temperature; and
(d) adding a desired quantity of an aqueous component, followed by mixing, to obtain a nanoemulsified formulation of hydrophobic active comprising particles having a particle size of between about 69 nm and about 212 nm.

18. The process according to claim 17, wherein the mixture of step (b) is heated at a temperature in the range of 50-200° C. to obtain solubilization of the hydrophobic biologically active material in the emulsifier.

19. The process according to claim 17, wherein the mixture of step (b) is subjected to sonication to obtain solubilization of the hydrophobic biologically active material in the emulsifier.

20. The process according to claim 17, wherein the mixture of step (b) is subjected to vortexing or ultra-high pressure homogenization to obtain solubilization of the hydrophobic biologically active material in the emulsifier.

21. A method of treating inflammation, osteoarthritis, allergy, obesity, neuro degenerative disorder(s), diabetes, cancer, cardio vascular disorder(s) and microbial disorder(s) comprising administering the sustained release nanoformulation according to claim 1, to a subject in need thereof.

* * * * *